United States Patent [19]
Morrison

[11] Patent Number: 5,935,856
[45] Date of Patent: *Aug. 10, 1999

[54] METHOD OF INHIBITING THE GROWTH OF BFGF-DEPENDENT NEOPLASTIC CELLS IN VITRO

[75] Inventor: Richard S. Morrison, Portland, Oreg.

[73] Assignee: Legacy Good Samaritan Hospital And Medical Center, Portland, Oreg.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/760,870

[22] Filed: Dec. 9, 1996

Related U.S. Application Data

[62] Division of application No. 08/382,521, Dec. 21, 1994, Pat. No. 5,583,116, which is a continuation of application No. 08/124,354, Sep. 20, 1993, abandoned, which is a continuation of application No. 07/818,898, Jan. 10, 1992, abandoned.

[51] Int. Cl.$^6$ .............................. C12N 5/10; C12N 15/18; A61K 48/00
[52] U.S. Cl. ........................ 435/368; 435/325; 536/24.5; 514/44
[58] Field of Search .......................... 536/24.5; 435/328, 435/325; 514/44

[56] References Cited

U.S. PATENT DOCUMENTS 5,583,116  12/1996  Morrison .................................... 514/44

OTHER PUBLICATIONS

Zhang, Hinton, Surnock, Couldwell, Malignant glioma sensitivity to radiotherapy, high–dose tamoxifen, and hypericin; corroborating climcal response in vitro: case report, Neurosurgery, Mar. 1996 38(3), pp. 587–590; discussion 590–1 (Abstract only).

Schadendorf, Worm, Algermissen, Kohlmus, Czarnetzki, "Chemosensitivity testing of human malignant melanoma. A retrospective analysis of clinical response and in vitro drug sensitivity, "Cancer, Jan. 1, 1994 73(1), pp. 103–108 (Abstract only).

Miura, Terashima, Yamazaki, Ikeyama, Sasaki, Taki, Eukuda, Ishikawa, Yogita, Tashiro, "Secondary hepatic resections in a case of sigmoid colon cancer with multiple liver metastasis (H3) after successful continuous hepatic artery infusion chemotherapy oriented by in vitro chemosensitivity test, " Gan to Kagaku Ryoho [Japanese journal of cancer and chemotherapy], Jun. 1997 24(8), pp. 1031–1034 (Abstract only).

Krasagakis, Almond–Roesler, Zouboulis, Tebbe, Wartenberg, Wolff, Orfanos, "Merkel cell carcinoma: report of ten cases with emphasis on clinical course, treatment, and in vitro drug sensitivity, "Journal of the American Academy of Dermatology, May 1997, 36(5 Pt 1), pp. 727–732 (Abstract only).

Sevin, B., Perras, J., "Tumor heterogeneity and in vitro chemosensitivity testing in ovarian cancer," Am. J. of Obstetrics and Gynecology, Apr. 1997 176(4), pp. 759–766, discussion 766–8 (Abstract only). (1997).

Antisense 97: A roundtable on the state of the industry. Nature Biotechnology 15, 519–524.

Alama, A., Barbieri, F. B. Cagnoli, M. and Schettini, G. (1997), Antisense oligonucleotides as therapeutic agents. Pharmacological Research 36, 171–178.

Bennett, C., Condon, T., Grimm, S., Chan, H. & Chiang, M. (1994), Inhibition of endothelial cell–leukocyte adhesion molecule expression with antisense oligonucleotides, Journal of Immunology 152, 3530–3540.

Geary, R.S., Leeds, J.M., Scott, P.H., Monteith, D.K. and Levin, A.A. (1997). Antisense oligonucleotide inhibitors for the treatment of cancer: 1. Pharmacokinetic properties of phosphorthioate oligodeoxynucleotides. Anti–cancer Drug Design 12, 383–393.

Kondo, Y., Kondo, S., Tanaka, Y., Haqqi, T., Barna, B. and Cowell, J. (1998), Inhibition of telomerase increases the susceptibility of human malignant glioblastoma cells to cisplatin–induced apoptosis. Ontogene 16, 2243–2248.

Pienat, F. (1996), Animal models of antisense oligonucleotides: lessons for use in humans. Molecular Medicine Today 250–257.

Temsamani, J. and Guinot, P. (1997). Antisense oligonucleotides: a new therapeutic approach. Biotecnol. Appl. Biochem. 26, 65–71.

Yacyshyn, B. R., Bowen–Yacyshyn, M.B., Jewell, L. Tami, J.A., Bennett, C.F. Kisner, D.L. and Shanahan, W.R. (1998). A placebo–controlled trial of ICAM–1 antisense oligonucleotide in the treatment of Crohn's disease. Gastroenterology 114, 1133–1142.

Becker et al., "Proliferation of human malignant melanomas is inhibited by antisense of oligonucleotides targeted against basic fibroblast growth factor," The EMBO Journal, vol. 8, No. 12, pp. 3685–3691, 1989.

Takahashi et al., "Inhibition of cell growth and tumorigenesis of human glioblastoma cells by a neutralizing antibody against human basic fibroblast growth factor," FEBS, vol. 288, No. 1, 2, pp. 65–71, 1991.

Lee et al., "Purification and Complementary DNA Cloning of a Receptor for Basic Fibroblast Growth Factor," Science, 245, pp. 57–60, Jul. 1989.

(List continued on next page.)

Primary Examiner—Johnny F. Railey, II
Attorney, Agent, or Firm—Stoel Rives LLP

[57] ABSTRACT

A method of inhibiting the growth of bFGF-dependent neoplastic cells is disclosed. The method includes the steps of accessing a selected colony of such cells and adding a bFGF-specific antisense primer to such colony. By performing the adding step, there is downregulating of the expression of colony-intracellular bound bFGF, and by performing the downregulating step, there is inhibiting of bFGF-promoted growth of cells in the colony.

8 Claims, 2 Drawing Sheets

OTHER PUBLICATIONS

Abraham et al., "Human basic fibroblast growth factor: nucleotide sequence and genomic organization," *The EMBO Journal*, vol. 5, No. 10, pp. 2523–2528, 1986.

Sommer et al., "An Amino–Terminally Extended and Post–Translationally Modified Form of a 25kD Basic Fibroblast Growth Factor," *Biochemical and Biophysical Research Communications*, vol. 160, No. 3, pp. 1267–1274, 1989.

Branch, TIBS 23:45–50 (1998).

"Antisense '97: A roundtable on the state of the industry," Nature Biotechnology 15:519–528 (1997).

Melton, "Injected anti–sense RNAs specifically block messenger RNA translation in vivo," *Proc. Natl. Acad. Sci. USA*, vol. 82, pp. 144–148, Jan. 1985.

Ch'ng et al., "Antisense RNA complementary to 3' coding and noncoding sequences of creatine kinase is a potent inhibitor of translation in vivo," *Proc. Natl. Acad. Sci. USA*, vol. 86, pp. 10006–10010, Dec. 1989.

Takahashi et al., "Gene expression of fibroblast growth factors in human gliomas and meningiomas: Demonstration of cellular source of basic fibroblast growth factor mRNA and peptide in tumor tissues," *Proc. Natl. Acad. Sci. USA*, vol. 87, pp. 5710–5714, Aug. 1990.

Hori et al., "Suppression of Solid Tumor Growth by Immunoneutralizing Monoclonal Antibody against Human Basic Fibroblast Growth Factor," *Cancer Research 51*, pp. 6180–6184, Nov. 15, 1991.

Takahashi et al., "Correlation of basic fibroblast growth factor expression levels with the degree of malignancy and vascularity in human gliomas," *J. Neurosurg.*, vol. 76, pp. 792–798, May 1992.

Paulus et al., "Localization of basic fibroblast growth factor, a mitogen and angiogenic factor, in human brain tumors," *Acta Neuropathologica*, 79, pp. 418–423, 1990.

Zagzag et al., "Immunohistochemical Localization of Basic Fibroblast Growth Factor in Astrocytomas," *Cancer Research 50*, pp. 7393–7398, Nov. 15, 1990.

Stefanik et al., "Acidic and Basic Fibroblast Growth Factors are Present in Glioblastoma Multiforme," *Cancer Research 51*, pp. 5760–5765, Oct. 15, 1991.

Maxwell et al., "Expression of Angiogenic Growth Factor Genes in Primary Human Astrocytomas May Contribute to Their Growth and Progression," *Cancer Research 51*, pp. 1345–1351, Feb. 15, 1991.

Akutsu et al., "Localization of Acidic and Basic Fibroblast Growth Factor mRNA in Human Brain Tumors," *Jpn. J. Cancer Res.*, 82, pp. 1022–1027, Sep. 1991.

Saxena et al., "Increased expression of genes from growth factor signaling pathways in glioblastoma cell lines," *Oncogene*, pp. 243–247, 1992.

Takahashi et al., "Gene Expression of Fibroblast Growth Factor Receptors in the Tissues of Human Gliomas and Meningiomas," *Biochemical and Biophysical Research Communications*, vol. 177, No. 1, pp. 1–7, 1991.

Rojanasakul, Advanced Drug Delivery Reviews 18:115–131 (1996).

Plenat, Molecular Medicine Today 2:250–257 (1996).

Palestine, Journal of the International Association of Physicians in AIDS Care 2(5):25–28 (1996).

Weiss, Science News 139:108–109 (1991).

Wickstrom, TIBTECH 10:281–287 (1992).

METHOD OF INHIBITING THE GROWTH OF BFGF-DEPENDENT NEOPLASTIC CELLS IN VITRO

This is a divisional of U.S. patent application Ser. No. 08/382,521, filed Dec. 21, 1994, now U.S. Pat. No. 5,583,116, which is a continuation of U.S. patent application Ser. No. 08/124,354, filed Sep. 20, 1993, now abandoned, which is a continuation of U.S. patent application Ser. No. 07/818,898, filed Jan. 10, 1992, now abandoned.

BACKGROUND OF THE INVENTION

The present invention relates to inhibiting the growth of bFGF-dependent neoplastic cells and more particularly, to reducing the growth of a specific type of neoplastic cells, i.e. human glioma cells.

Neoplasm, or aberrant, uncontrolled growth patterns of abnormal tissue is an undesirable condition. Substantial research has been performed on neoplastic cells with the ultimate goal being to inhibit or reduce growth of such cells.

The present invention will be described in the context of human glioma cells but may be applicable to other neoplastic cells as well. Also by way of background, basic fibroblast growth factor will be discussed briefly because the present invention centers on the use of bFGF-specific antisense primer (also referred to herein as bFGF-specific oligonucleotide).

It is known that bFGF is a heparin-binding, multifunctional protein that has until now been recognized primarily for its mitogenic and angiogenic properties. On the basis of cell culture studies, bFGF has been shown to be mitogenic for a wide range of cell types derived from mesoderm and neuroectoderm. In addition to the many in vitro studies performed with bFGF, it is also active in numerous in vivo models of angiogenesis and wound healing. bFGF has been identified in many normal and malignant tissues and at several developmental time points, implying that it may play a role in normal tissue function, embryonic development and neoplastic progression.

The mammalian central nervous system (CNS) is a particularly abundant source of bFGF. Substantial quantities of bFGF have been purified from whole brain extracts, hypothalamus and retina. Despite its abundance in neural tissue, a precise cellular localization for bFGF synthesis in brain has not been unequivocally determined. bFGF immunoreactivity has been localized to neurons, in vitro and in vivo by immunocytochemical analysis. In a more recent survey, enhanced bFGF immunoreactivity was observed in brain regions enriched in neurons. In contrast, bFGF has also been identified in cultured mouse cerebellar astroglia and in reactive rat astrocytes surrounding a focal suction wound to the brain.

Based on the above-described studies, I concluded that astrocytes, or star-shaped neurological cells, may represent a potential source of bFGF expression in the CNS under appropriate circumstances. This conclusion is consistent with the recent identification of bFGF in human glial tumors and in transformed human glial cell lines. In addition to expressing bFGF, human glioma cells respond to it with increased proliferation, suggesting that bFGF may be involved in an autocrine pathway regulating glioma growth and invasion.

Due to its multifunctional properties bFGF could potentially influence glioma development by directly stimulating tumor cell growth or by promoting tumor vascularization. bFGF and related members of the FGF family have been implicated in the autocrine regulation of human tumor growth based partly on transfection studies with bFGF expression vector, which result in amplified autocrine growth in monolayer culture and soft agar.

The overexpression of growth factors and their receptors has been implicated in the genesis and maintenance of a variety of human neoplasms. The putative growth factor receptor c-neu (c-erbB-2), has been detected in a significant number of human breast carcinomas while the epidermal growth factor (EGF) receptor is amplified in approximately 30–40% of human gliomas. Amplication of bFGF-related int-2 and host genes has also been observed in a small percentage of breast tumors.

An object of the present invention is to alter bFGF expression in human glioma cells as a way of ultimately inhibiting growth of such cells.

Another object of the present invention is to alter bFGF expression in human glioma cells as a way of ultimately changing the malignancy behavior of such cells.

SUMMARY OF THE INVENTION

The present invention takes the form of a method of inhibiting the growth of bFGF-dependent neoplastic cells. Human glioma cells are an example of such bFGF-dependent neoplastic cells because elevated levels of bFGF have recently been described in human glioma cell lines. The high degree of vascularity and invasiveness which characterize human gliomas suggest that activated expression of bFGF or similar proteins, may be related to the neoplasm.

The method of the present invention includes the steps of accessing a selected colony or colonies of bFGF-dependent neoplastic cells, adding a bFGF-specific antisense primer to such colony, by such adding step, downregulating the expression of colony-intracellular-bound bFGF, and as a consequence of the downregulating step, inhibiting bFGF-promoted growth of cells in the colony(ies).

By and as a consequence of performing the inhibiting step, the method of the present invention also includes reducing the invasion and migration capabilities of cells in the colony.

The present invention shows that basic fibroblast growth factor, a potent mitogenic and angiogenic protein, is also a regulator of tumor cell growth.

These and additional objects and advantages of the present invention will be more readily understood after a consideration of the drawings and the detailed description of the preferred embodiment.

DETAILED DESCRIPTION OF THE PREFERRED MODE OF PRACTICING THE INVENTION

As will be shown below, bFGF expression can be altered in human glioma cells following application of bFGF-specific antisense oligonucleotides. bFGF expression occurs in both non-transformed and transformed human glial cells. However, only the growth of transformed human glial cells is suppressed in the presence of bFGF-specific antisense primers. Thus, while bFGF may normally be expressed by astrocytes, elevated levels or aberrant forms of bFGF may predispose astrocytes to uncontrolled cell growth.

Also, in connection with the present description, I will refer to groups of human glioma cells as colonies of such cells. Also, it should be understood that use of the term colony-intracellular-bound bFGF refers to bFGF present in the cells as opposed to extracellular bFGF.

Referring to Table I below, oligonucleotide primers corresponding to different sites of the sense or antisense bFGF mRNA were synthesized in an unmodified form. These primers were directed against either the translation initiation site (AUG codon, referred to AS-1), or codon 60, the first splice donor-acceptor site (referred to as AS-2). Antisense primer corresponding to the initiation site of the B-chain of human platelet derived growth factor (PDGF) was also synthesized. Despite extensive sequence similarity between bFGF and other members of the FGF family, the sequences of the primers were sufficiently divergent from the other related gene sequences to prevent inappropriate duplex formation.

Figure 1:
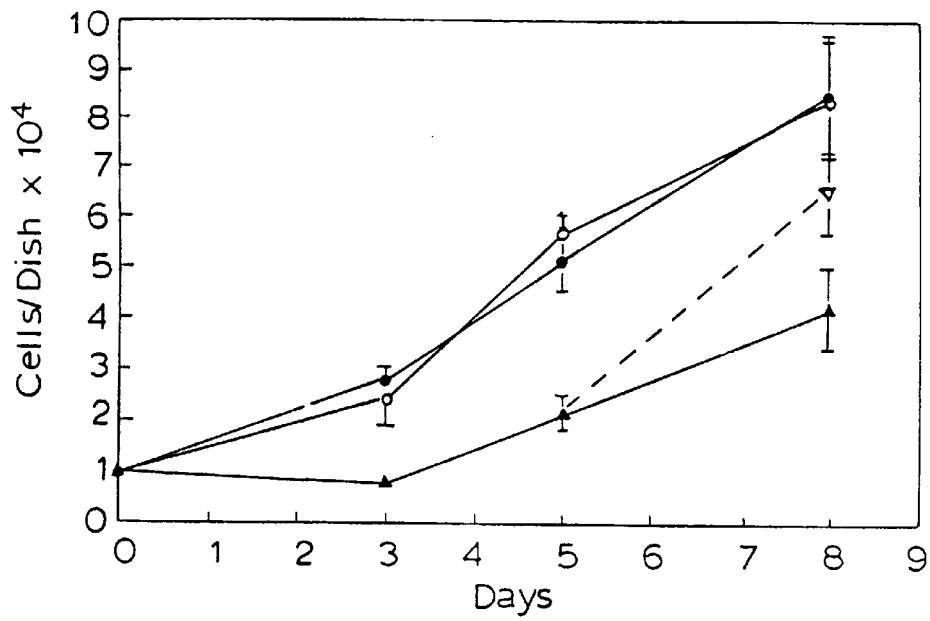
FIG. 1 is a graph of human-glioma-cell concentration (ordinate) vs. time (abscissa) showing inhibition of glioma cell growth over time in the presence of bFGF-specific antisense oligonucleotide primer.
Figure 2:
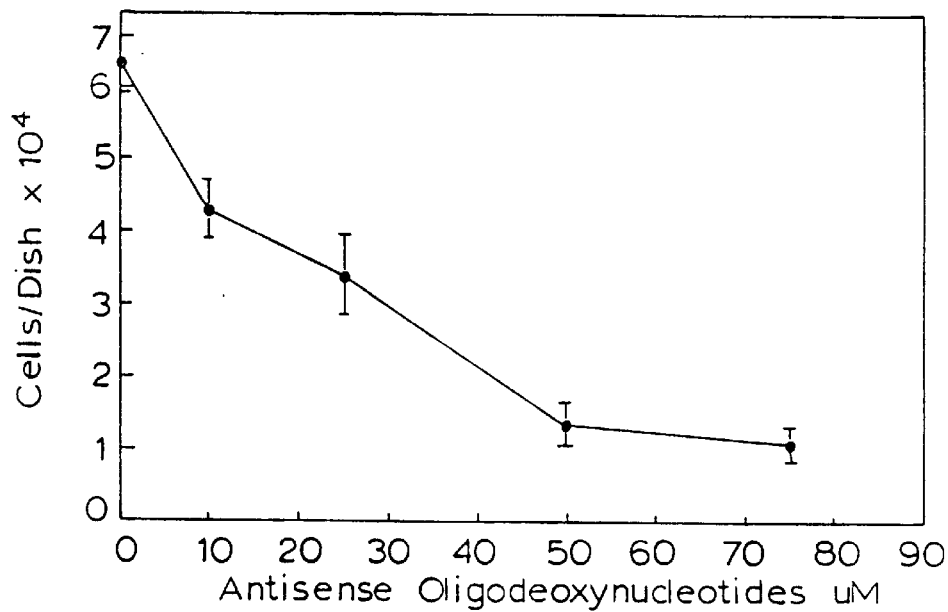
FIG. 2 is a graph of human-glioma-cell concentration (ordinate) vs. bFGF-specific-antisense-oligonucleotide-primer concentration (abscissa) showing the inhibition of glioma cell growth with increasing concentrations of such primer.

Referring to FIG. 2, the growth response of SNB-19 cells is shown as a function of bFGF-specific antisense oligonucleotide primer (SEQ ID NO:3) (AS-2) concentration. SNB-19 cells were plated and maintained as described in connection with FIG. 1. Eighteen hours after plating, the cells were washed 3 times with PBS and converted to SFM with varying concentrations of AS-2 primer (SEQ ID NO:3). Eight days after conversion to SFM plus the antisense primer, cells were trypsinized and counted using a hemocytometer. Two wells were used per concentration and the data represent the average of two separate experiments±standard deviation.

Figure 3:
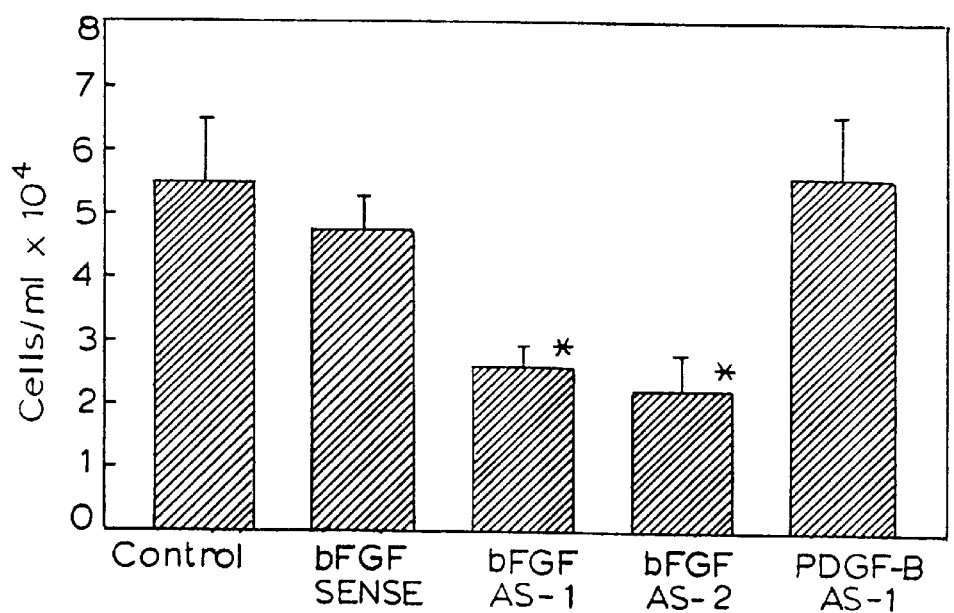
FIG. 3 is a bar graph of human-glioma-cell concentration (ordinate) vs. concentration of various sense and antisense primers (abscissa) showing that human-glioma-cell concentration is inhibited by various bFGF-specific antisense primers more than it is inhibited by sense primers or non-FGF antisense primers.

Referring to FIG. 3, the growth response of SNB-19 cells is shown relative to bFGF-specific and unrelated antisense oligonucleotide primers. SNB-19 cells were plated and maintained as described in the legend to FIG. 1. Eight hours after plating, the cells were washed 3 times with PBS and converted to SFM alone (control), SFM plus bFGF-specific sense primer (SEQ ID NO:1) (S-2, 35 μM), SFM plus bFGF-specific antisense primer (SEQ ID NO:2) AS-1 (35 μM, SFM plus bFGF-specific antisense primer (SEQ ID NO:3) AS-2 (35 μM), and SFM plus PDGF-B-chain-specific antisense primer (SEQ ID NO:4) (35 μM). Eight days after conversion to SFM plus the respective oligonucleotide primer, cells were trypsinized and counted using a hemocytometer. Two wells were used per condition and the data represent the average of tree separate experiments±standard deviation. The * symbols mean that AS-1 (SEQ ID NO:2) and AS-2 (SEQ ID NO:3) antisense primers differ significantly from control bFGF (SEQ ID NO:1) sense and PDGF-B (SEQ ID NO:4) at $P<0.01$.

TABLE I

Location and Structure of Oligonucleotide Primers
It is known that two introns interrupt the human bFGF coding sequence. The first intron interrupts the coding sequence at codon 60. Sense and antisense primers corresponded to codons 58–62 which span the first splice-donor acceptor site. The start site refers to the translation initiation (ATG) site. h-bFGF refers to human basic fibroblast growth factor and h-PDGF-B refers to human platelet derived growth factor-B chain.

| Growth Factor | Primer | Location | Sequence |
|---|---|---|---|
| h-bFGF | Sense (SEQ ID NO: 1) | Codon 58 | 5'-CCT—CAC—ATC—AAG—CTA-3' |
| h-bFGF | Antisense (AS-1) (SEQ ID NO: 2) | Codon 58 | 5'-TAG—CTT—GAT—GTG—AGG-3' |
| h-bFGF | Antisense (AS-2) (SEQ ID NO: 3) | Start site | 5'-GGC—TGC—CAT—GGT—CCC-3' |
| h-PDGF-B | Antisense (SEQ ID NO: 4) | Start site | 5'-GCG—ATT—CAT—GCC—GAC-3' |

Referring to FIG. 1, SNB-19 cell lines were derived from a high grade glioblastoma. The derivation of this tumor was confirmed by the usual histological analysis. The glioma cell line expressed the astrocyte antigen, gliofibrillary acidic protein (GFAP), confirming its glial origin. The glioma cell line was maintained following the usual methods and was Mycoplasma free.

Still referring to FIG. 1, SNB-19 cells were plated at a density of $1\times10^4$ cells per 2.1 cm$^2$ well in serum-supplemented medium (10% FCS). Eighteen hours later the cells were washed 3 times with PBS and converted to SFM alone (•), SFM plus 25 μM sense primer (SEQ ID NO:1) (○) or SFM plus 25 μM antisense primer (SEQ ID NO:3) AS-2(▲). One set of wells was maintained in medium with antisense primer (SEQ ID NO:3) AS-2 (25 μM) for five days, washed 3 times with PBS and converted back to SFM alone (▽). At the appropriate time points the cells were washed 2 times with PBS, trypsinized and counted using a hemocytometer. The data represents the number of cells per dish±standard deviation. Duplicate wells were used for each time point and the results represent the average of two separate experiments.

Referring to below-identified Table II, the lack of growth inhibition observed from the bFGF-specific sense primer (SEQ ID NO:1) and the PDGF-B-chain-specific antisense primer (SEQ ID NO:4) suggested that the inhibitory effect of the bFGF-specific antisense primers was (SEQ ID NO:2, SEQ ID NO:3) related to specific alterations in the bFGF expression. I investigated this possibility by measuring bFGF protein in SNB-19 cells using known slot-blot immuno-detection techniques. bFGF protein was quantitated by slot-blot analysis against a standard human recombinant bFGF curve. The monoclonal antibody used in the detection of bFGF was previously shown to be specific for human bFGF and did not cross-react with human acidic FGF. Furthermore, the antibody recognized the appropriate molecular weight forms of bFGF in SNB-19 cells as judged by the Western blot analysis.

Still referring to below-identified Table II., SNB-19 cells grown in serum-free medium until approximately 75% confluent exhibited 5.56 ng of bFGF/μg of protein. The sense strand primer (SEQ ID NO:1), which did not affect SNB-19 cell growth, correspondingly had no effect on SNB-19 bFGF content. In marked contrast, antisense primer (SEQ ID NO:2) AS-1 (35 μM) significantly reduced the FGF expression in SNB-19 cells. The 67% reduction in bFGF content was parallelled by a 55% reduction in cell number (undepicted) leading to my conclusion that inhibition of SNB-19 cell growth was directly related to the loss of bFGF.

TABLE II

Influence of bFGF Sense and Antisense Oligonucleotides on the bFGF Content of SNB-19 Cells

| Condition | Conc.(μM) | bFGF Content | % Reduction |
|---|---|---|---|
| Control | — | 5.71 ± 0.37 | — |
| Sense Primer (SEQ ID NO: 1) | 35 | 6.44 ± 0.12 | 0 |
| Antisense Primer (SEQ ID NO: 2) | 35 | 1.87 ± 0.31* | 67.25 |

SNB-19 cells were plated at a density of $5 \times 10^5$ cells per 21 cm$^2$ plate in serum supplemented medium (10% FCS). Eighteen hours later the cells were washed 3 times with PBS and converted to SFM alone (control), SFM plus bFGF-specific sense primer (SEQ ID NO: 1) (35 μM) or SFM plus bFGF-specific antisense primer (SEQ ID NO: 2) AS-1 (35 μM).
Four days after conversion to SFM plus primers the cells were trypsinized and counted. Equal numbers of cells were removed from each treatment ($3 \times 10^5$ per plate) and cell extracts were prepared following the usual methods.
Extracts were evaluated for protein content and administered to nitrocellulose using known slot-blot apparatus. bFGF immunoreactivity was visualized using the usual alkaline phosphatase-conjugated secondary antibodies.
The nitrocellulose was washed extensively with water to stop the color reaction, dried and scanned using a densitometer. The bFGF content of the various extracts was determined by comparison with a human-recombinant bFGF standard curve.
The data are expressed as the content of bFGF per μg of extract protein. All immunoreactivity fell within the linear range of the human recombinant-bFGF standard curve.
Different amounts of extract were also evaluated to confirm that the amount of extract added to the slot-blot was not saturating. The extract from a single plate was tested in duplicate.
The data represent the average of four separate determinations ± standard deviation. The * symbol means that bFGF content of the antisense primer differed from control and sense primer at $P < 0.01$.

Bringing together the procedures discussed above in connection with the figures and tables, the influence of endogenous bFGF on glioma cell growth in vitro was evaluated by accessing a selected colony of such cells, adding a bFGF-specific antisense primer to such colony (such as (SEQ ID NO:2) AS-1 or (SEQ ID NO:3) AS-2 of Table I), by such adding, downregulating the expression of colony-intracellular-bound bFGF, and as a consequence of the downregulating step, inhibiting bFGF-promoted growth of cells in the colony.

With respect to the downregulating step, the addition of 50 μM bFGF-specific antisense primer (SEQ ID NO:2, SEQ ID NO:3) to the human glioma cell line SNB-19 resulted in an 80% inhibition in glioma growth. This effect was saturable and specific. Antisense primers (SEQ ID NO:2, SEQ ID NO:3) directed to two different sites of bFGF mRNA were effective in suppressing SNB-19 growth, whereas sense strand primer (SEQ ID NO:1) was ineffective. Furthermore, only the antisense primer (SEQ ID NO:2, SEQ ID NO:3) significantly reduced the specific activity of bFGF protein in SNB-19 cell extracts. Neither antisense (SEQ ID NO:2, SEQ ID NO:3) or sense primers (SEQ ID NO:1) inhibited the growth of non-transformed human glia. bFGF mRNA was detected in both transformed and non-transformed human glia by polymerase chain reaction (PCR) analysis showing that alterations in bFGF isoform content, concentration or activity may be specifically related to abnormal growth control in human gliomas.

The invention may also be thought of as a method of changing the malignancy behavior of glioma cells by selecting a colony of such cells, adding a preselected amount of bFGF-specific antisense primer (SEQ ID NO:2, SEQ ID NO:3) to such colony to modulate bFGF expression in such cells, and by said adding, changing the malignancy behavior of such cells.

The invention may also be expressed in a third way as a method of reducing growth of glioma cells by selecting a colony of such cells, adding a preselected amount of bFGF-specific antisense oligodeoxynucleotides (SEQ ID NO:2, SEQ ID NO:3) to modulate bFGF expression in such cells by reducing such expression, and by such adding, reducing growth of such cells.

The present invention also shows that bFGF may confer autonomous cell growth on neoplastic glial cells. Human glioma cells have recently been shown to express bFGF mRNA, bFGF protein and high-affinity-bFGF receptors. Thus, all of the components necessary for a bFGF autocrine pathway exist in some glioma cells. Addition of exogenous bFGF to human glioma cells in culture enhances cell proliferation. Malignant glioma cells grow exceptionally well in serum-free medium and in soft agar which could reflect the expression of high levels of intracellular bFGF. A correlation between intracellular bFGF content and the degree of malignancy in gliomas night explain why highly malignant gliomas are less responsive to exogenous bFGF compared to normal astrocytes and benign gliomas.

The idea that glioma cell growth is promoted by an autocrine pathway involving bFGF was tested by selectively reducing bFGF expression in SNB-19 glioma cells using bFGF-specific antisense primers (SEQ ID NO:2, SEQ ID NO:3). The addition of the primers (SEQ ID NO:2, SEQ ID NO:3) significantly attenuated SNB-19 cell growth and appeared to be specific. The specificity of the antisense primers (SEQ ID NO:2, SEQ ID NO:3) was supported by the following observations: 1) a bFGF-specific sense strand primer (SEQ ID NO:1) lacked growth inhibitory activity, 2) growth inhibition was observed with two different bFGF-specific antisense primers (SEQ ID NO:2, SEQ ID NO:3) corresponding to different sites of the bFGF mRNA, 3) a PDGF-B chain-specific antisense primer (SEQ ID NO:4) also lacked growth inhibitory activity, 4) growth inhibition was dose-dependent and saturable, 5) bFGF-specific sense primers (SEQ ID NO:1) did not effect bFGF content in SNB-19 cells, while bFGF-specific antisense primers (SEQ ID NO:2, SEQ ID NO:3) reduced the bFGF content of SNB-19 cells by 67% and 6) bFGF-specific antisense primers (SEQ ID NO:2, SEQ ID NO:3) did not inhibit the growth of non-transformed cells. While these results do not rule out a contribution by other growth factors to the growth of SNB-19 cells, they clearly demonstrate that endogenous bFGF promotes SNB-19 cell growth.

The lack of growth inhibition observed with antisense primers (SEQ ID NO:2, SEQ ID NO:3) on non-transformed human glia further suggests that bFGF expression is relevant to the growth of human gliomas. Non-transformed astrocytes express bFGF mRNA as shown by PCR analysis. Therefore, the mere presence of bFGF is not sufficient to promote abnormal cellular growth. As described, altered forms, concentration and activity may contribute to bFGF-dependent growth in gliomas.

In summary, the present invention shows that human glial cells have the capacity to express bFGF and that alterations in FGF expression plays a role in the development and progression of human gliomas. bFGF-specific antisense primers (SEQ ID NO:2, SEQ ID NO:3) have proven an effective tool to modulate bFGF expression in glioma cells and may eventually be applied to control the growth of these cells. Since bFGF expression is observed in both transformed and non-transformed astrocytes, characterizing the bFGF receptor and bFGF isoforms in these cells may shed light on the role of bFGF in neoplastic transformation.

While the present invention has been shown and described with reference to the foregoing preferred embodiment, it will be apparent to those skilled in the art that other changes in form and detail may be made therein without departing from the spirit and scope of the invention as defined in the appended claims.

It is desired to secure and claim by Letters Patent:

1. A method of inhibiting angiogenicity of glioma cells comprising:

accessing a selected colony of such cells, adding a preselected amount of bFGF-specific antisense primer to such colony in vitro to modulate bFGF expression in such cells in vitro, and by said adding, inhibiting the angiogenicity of such cells in vitro.

2. A method to alter bFGF expression in developing glial cells of neuronal tissues comprising:

accessing a selected colony of such cells, adding a preselected amount of bFGF-specific antisense primer to such colony in vitro to modulate bFGF expression in such cells in vitro, and by said adding, inhibiting the growth of such cells in vitro.

3. The method of claim 1 wherein the antisense primer has the sequence given in SEQ ID NO: 2 or SEQ ID NO: 3.

4. The method of claim 1 in which the glioma cells are human glioma cells.

5. The method of claim 4 wherein the antisense primer has the sequence given in SEQ ID NO: 2 or SEQ ID NO:3.

6. The method of claim 2 in which the glial cells are human glial cells.

7. The method of claim 6 wherein the antisense primer has the sequence given in SEQ ID NO:2 or SEQ ID NO:3.

8. The method of claim 2 wherein the antisense primer has the sequence given in SEQ ID NO:2 or SEQ ID NO:3.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

CCTCACATCA AGCTA                                                                15

(2) INFORMATION FOR SEQ ID NO:2:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:2:

TAGCTTGATG TGAGG                                                                15

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:3:

GGCTGCCATG GTCCC                                                                15

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:4:

GCGATTCATG CCGAC                                                                                                   15